United States Patent [19]
Estis et al.

[11] Patent Number: 5,026,557
[45] Date of Patent: Jun. 25, 1991

[54] ADJUVANT COMPOSITION

[75] Inventors: Leonard Estis, Upton, Mass.; Phillip Livingston, New York, N.Y.

[73] Assignee: The Liposome Company, Inc., Princeton, N.J.

[21] Appl. No.: 483,263

[22] Filed: Feb. 14, 1990

Related U.S. Application Data

[63] Continuation of Ser. No. 94,564, Sep. 9, 1987, abandoned.

[51] Int. Cl.$^5$ .............................................. A61K 37/22
[52] U.S. Cl. ...................................... 424/450; 424/88
[58] Field of Search ................................. 424/450, 88

[56] References Cited

U.S. PATENT DOCUMENTS

| | | | |
|---|---|---|---|
| 004,762 | 1/1887 | Cullis et al. | 424/223 |
| 036,980 | 4/1887 | Suddith | 424/223 |
| 788,017 | 10/1885 | Cullis et al. | 424/223 |
| 4,053,585 | 10/1977 | Allsion et al. | 424/92 |
| 4,148,876 | 4/1979 | Almeida et al. | 424/89 |
| 4,199,565 | 4/1980 | Fullerton | 424/89 |
| 4,557,931 | 12/1985 | Irie et al. | 424/88 |
| 4,826,687 | 5/1989 | Nerome et al. | 424/450 |

FOREIGN PATENT DOCUMENTS

| | | |
|---|---|---|
| 0011549 | 5/1980 | European Pat. Off. |
| 0047480 | 3/1982 | European Pat. Off. |
| WO89/05633 | 6/1989 | World Int. Prop. O. |

OTHER PUBLICATIONS

Alving, Carl R. et al., "Effectiveness of Liposomes as Potential Carriers of Vaccines: Applications to Cholera Toxin and Human Malaria Sporozoite Antigent", *Vaccine* 4:166–172 (1986).
Benjamins, J. A. et al., "Production and Characterization of High Titer Antibodies to Galactocerebroside", *J. Neuroimmuno.*, 14:325–338 (1987).
Brade, Lore et al., "Immunogenicity and Antigenicity of Synthetic *Escherichia Coli* Lipid A", *Infection and Immunity* 51:110–114 (1986).
Claassen, E. et al., "Immunomodulation with Liposomes: the Immune Response Elicited by Liposomes with Entrapped Dichloromethylene-Diphosphonate and Surface-Associated Antigen or Hapten", *Immunol.*, 60:509–515 (1987).
Davis, D. et al., "Liposomes as Adjuvants with Immunopurified Tetanus Toxoid; The Immune Response", *Immunol. Lett.*, 14:341–349 (1087).
Davis, D. et al., "Liposomes as Immunological Adjuvants in Vaccines: Studies with Entrapped and Surface Linked Adjuvants", *Biochem. Soc. Trans.*, 14:1036–1037 (1986).
Davis, D. et al., "Liposomes as Adjuvants with Immunopurified Tetanus Toxoid: Influence of Liposomal Characteristics", *Immunol.*, 61:229–234 (1987).
Gerlier, D. et al., "Liopsomes as a Tool to Study the Role of Membrane Presentation in the Immunogenicity of a MuLV-Related Tumor Antigen", *J. Immunol.*, 131:485–490 (1983).
Gregoriadis, G. et al., "Liposomes as Immunological Adjuvants: Antigen Incorporation Studies", *Vaccine*, 5:145–151 (1987).
Jiskoot, Wim et al., "Immunogenic Activity of Genococcal Protein I in Mice with Three Different Lipoidal Adjuvants Delivered in Liposomes and in Complexes", *Infection and Immunity*, 54:333–338 (1986).
Latif, N. A. et al., "The Effect of Surface-Coupled Antigen of Liposomes in Immunopotentiation", *Immunol. Lett.*, 15:45–51 (1987).
Livingston, P. O. et al., "Approaches to Augmenting the Immunogenicity of the Ganglioside GM2 in Mice: Purified GM2 is Superior to Whole Cells", *J. Immunol.*, 138:1525–1529 (1987).
Matei, "Ligia, et al., Liposomes as Immunological Adjuvants for Lysozyme Intragastrically Administered into Rabbits. Serum Immunity Potentiation", *Rev. Roum. Biochin*, 23:203–209.
Naylor et al., "In Vivo Induction of Anti-Herpes Simplex Virus Immune Response by Type 1 Antigens and Lipid A Incorporated into Liposomes", *Infection and Immunity* 36:1209–1216 (1982).
Phillips, S. Michael et al., "Release of Xenotropic Type C RNA Virus in Response to Lipopolysaccharide: Activity of Lipid-A Portion upon B Lymphocytes", *J. Immunol.*, 116:1123–1128 (1976).
van Rooijen, Nico et al., "Use of Liposomes as Biodegradable and Harmless Adjuvants", *Methods in Enzymology*, 93:83–95 (1983).
Zigterman, Guy J. W. J. et al., "Immunomodulating Properties of Substances to be Used in Combination with Liposomes", *Int. Arch Allergy Appl. Immun.*, 81:245–252 (1986).
Zigterman, J. W. J. et al., "Adjuvant Effects of Nonionic Block Polymer Surfactants on Liposome-Induced Humoral Immune Response", *J. Immunol.*, 138:220–225 (1987).
Almeida et al., "Formation of Virosomes from Influenza Subunits and Liposomes", 1975, The Lancet, pp. 899–901.
Alving, Chapter 6 of Liposomes, Marcel Dekker, N.Y., Marc Ostro, Ed., pp. 195–218.

(List continued on next page.)

*Primary Examiner*—Theodore Morris
*Assistant Examiner*—David M. Brunsman
*Attorney, Agent, or Firm*—Allen Bloom; Thomas M. Saunders; Ronald G. Ort

[57] ABSTRACT

An adjuvant composition comprising a small liposome with incubation associated immuno-potentiator such as Lipid A, said composition with incubation associated antigen, and method of preparation and use.

29 Claims, No Drawings

OTHER PUBLICATIONS

Bormann et al., "Synthetic Peptides Mimic the Assembly of Transmembrane Glycoproteins", Chem. Abs. 110(23)208025j.

Francis et al., "Immunological Priming with Synthetic Peptides of Foot and Mouth Disease Virus", 1985, *J. Gen. Virol.* 66:2347-2354.

Humphries, "Evidence for Direct Control of an in Vitro Plaque-Forming Cell Response by Quantitative Properties of Intact, Fluid, Haptenated Liposomes: a Potential Model System for Antigen Presentation by Macrophages", 1981, *J. Immunol.* 126(2):688-692.

Kraaijeveld et al., "The Effect of Liposomal Charge on the Neutralizing Antibody Response Against Inactivated Encephalomyocarditis and Semliki Forest Viruses", 1984, *Clin. Immunol.* 56:509-514.

Naylor et al., "In Vivo Induction of Anti-Herpes Simplex Virus Immune Response by Type 1 Antigens and Lipid A Incorporated into Liposomes", 1982, *Infec. and Immun.* 36(3):1209-1216.

Pierce et al., "Enhancement by Lipid A of Mucosal Immunogenicity of Liposome-Associated Cholera Toxin", 1984, *Rev. Infect. Dis.* 6(4):563-566.

Siddiqui et al., "Vaccination of Experimental Monkeys Against Plasmodium Falciparum: A Possible Safe Adjuvant", 1978, *Sci.* 201:1237-1239.

Tan et al., "Effect of Interleukin-2 on the Immunoadjuvant Action of Liposomes", 1989, *Biochem. Soc. Trans.* 17:693-694.

Tan et al., "Incorporation of Reconstituted Influenza Virus Enveloped Into Liposomes:Studies of the Immune Response in Mice", 1989, *Biochem. Soc. Trans.* 17:129-130.

van Houte et al., "Characterization of Immunogenic Properties of Haptenated Liposomal Model Membranes in Mice I. Thymus Independence of the Antigen", 1979, *Immunol.* 37:505-514.

van Houte et al., "Characterization of Immunogenic Properties of Haptenated Liposomal Model Membranes in Mice V. Effect of Membrane Composition on Humoral and Cellular Immunogenicity", 1981, *Immunol.* 44:561-568.

van Rooijen et al., "Liposomes in Immunology:Evidence That Their ADjuvant Effect Results from Surface Exposition of the Antigens", 1980, *Cell. Immunol.* 49:402-407.

Walden et al., "Induction of REgulatory T-Lymphocyte Responses by Liposomes Carrying Major Histocompatibility Complex MOlecules and Foreign Antigen", 1985, *Nature* 315(23):327-329.

Jin-Zhu Yin et al., "Effect of Various Adjuvants on the Antibody Response of Mice to Pheumococcal Polysaccharides", 1988, *J. Biol. Res. Mod.* 8:190-205.

Kramp et al., "Liposomal Enhancement of the Immunogenicity of Adenovirus Type 5 Hexon and Fiber Vaccines", 1979, *Infection and Immunity* 25:771-773.

ADJUVANT COMPOSITION

This application is a continuation of Ser. No. 07/094,564, filed Sept. 9, 1987, now abandoned.

FIELD OF THE INVENTION

This invention involves an adjuvant composition comprising a small liposome with incubation associated immuno-potentiator such as Lipid A, said composition with incubation associated antigen, and method of preparation and use.

BACKGROUND OF THE INVENTION

Gangliosides are cell surface glycosphingolipids expressed abundantly by most malignant melanomas and other cancers of neuroectodermal origin. Three gangliosides, the disialogangliosides GD3 and GD2 and the monosialoganglioside GM2, have proven to be of particular interest to tumor immunologists for a variety of reasons. GD3 is recognized by several mouse monoclonal antibodies but by no sera or monoclonal antibodies of human origin. GD2 and GM2 are reactive with sera from some melanoma patients and some normal donors and have recently been detected by mouse and human monoclonal antibodies. From the pattern of cellular distribution in normal and malignant tissues, it appears that GD3, GD2, and GM2 have the characteristics of differentiation antigens of neuroectodermal origin. Interest in these antigens was intensified by the observation that there was regression of melanoma and neuroblastoma metastases in some patients treated with anti-GD3 and anti-GD2 mouse monoclonal antibodies indicating that cell surface gangliosides may be targets for cancer therapy.

Gangliosides play critical roles in cell-cell interactions as differentiation markers and receptors for toxins, hormones and other factors. Malignant transformation frequently results in changes in ganglioside pattern and the importance of ganglioside for detection and treatment of cancer has recently been established. However, gangliosides are rarely immunogenic, thwarting attempts at active immunization or production of monoclonal antibodies. Association of poorly immunogenic or tolerated antigens with immunostimulating complexes is a method of augmenting immunogenicity. GM2 is used as a model for all gangliosides. The relative immunogenicity of the different ganglioside preparations may be determined in mice and methods to further increase their immunogenicity in various types of vaccines determined. Approaches shown to be optimal for GM2 are applicable to GD2, GD3, GM3 analogues and derivatives thereof (including O-acetyl GD3) and other gangliosides.

It has now been discovered that a "small" liposome, that is a liposome with a diameter of about 500 nm or less, with incubation associated immuno-potentiators such as Lipid A is an improved adjuvant, as measured by the anti-GM2 titer of animal sera obtained after inocculation with such liposomes containing incubation associated Lipid A and GM2.

SUMMARY OF THE INVENTION

This invention includes an adjuvant comprising a small liposome and incubation associated immuno-potentiator such as Lipid A. Particularly included are liposomes of about 100 nm in diameter, the liposome being a unilamellar vesicle, Lipid A present in at least about 5 ug/mg liposome lipid, Lipid A present in at least about 25 ug/mg liposome lipid or the lipid comprising phosphatidylcholine.

In one embodiment the adjuvant composition further comprises an incubation associated antigen such as a ganglioside, particularly GM2, GD2, or GD3. In a particular embodiment GM2 is present in an amount of at least about 3 ug/mg liposome lipid, or at least about 10 ug/mg liposome lipid, or at least about 30 ug/mg liposome lipid. This composition of adjuvant and GM2 liposome lipid, in a pharmaceutical dosage form, comprises at least about 50 to about 500 ug GM2, and preferably at about 100 to 300 ug GM2.

This invention also comprises the adjuvant composition of the process of combining by incubation association unilamellar vesicles with an immuno-potentiator such as Lipid A. In one embodiment the composition of the process further comprises combining by incubation association with a unilamellar vesicle an antigen, such as a ganglioside, such as GM2, GD2, or GD3.

This invention additionally includes a method of preparing an adjuvant composition comprising combining by incubation association a small liposome with an immuno-potentiator such as Lipid A. In a further embodiment the method comprises combining by incubation association with the liposome an antigen, such as a ganglioside, such as GM2, GD2, or GD3. In an embodiment of this method the small liposome is a unilamellar vesicle.

This invention yet further includes a method of augmenting an immune response in an animal comprising administering an adjuvant composition comprising a small liposome and incubation associated immuno-potentiator such as Lipid A, particularly wherein the Lipid A is present in at least about 5 ug/mg liposome lipid, or at least about 25 ug/mg liposome lipid. In one embodiment the adjuvant further comprises an antigen, such as a ganglioside, such as GM2, GD2, or GD3.

DETAILED DESCRIPTION OF THE INVENTION

The monosialoganglioside GM2 is obtained in purified form from a number of sources (e.g., Supelco, Inc., Bellefonte, Pa.). GD2 and GD3 are similarly commercially available. The designations GM2, GD2, and GD3 will be understood to include analogues and derivatives thereof, with particular reference to monophosphoryl GM2, and O-acetyl GD3.

Lipid A is the lipid fraction of endotoxin (lipopolysaccharide). Generally, this is obtained from gram negative bacteria. As used herein Lipid A also refers to analogues and derivatives of Lipid A. Highly purified Lipid A in the monophosphorylated form ("MP Lipid A") (derived from Salmonella lipopolysaccharide) may be obtained from Ribi Immunochem, Inc. (Hamilton, Mont.). The monophosphoryl form of Lipid A is described as less toxic than the unphosphorylated form.

Lipid A will be understood to be part of a group of compositions termed herein "immuno-potentiators" that augment the effectiveness of adjuvants. Other examples of immuno-potentiators are killed tuberculin bacillus for complete Freunds adjuvant, and lymphokines such as IL-1 or IL-2.

Liposomes are completely closed lipid bilayer membranes containing an entrapped aqueous volume. Liposomes may be unilamellar vesicles (possessing a single bilayer membrane) or multilameller vesicles (onion-like structures characterized by multiple membrane bilayers, each separated from the next by an aqueous layer). The bilayer is composed of two lipid monolayers having a hydrophobic "tail" region and a hydrophilic "head" region. The structure of the membrane bilayer is such that the hydrophobic (nonpolar) "tails" of the lipid monolayers orient toward the center of the bilayer while the hydrophilic "head" orient towards the aqueous phase.

The original liposome preparation of Bangham, et al. (*J. Mol. Biol.*, 1965, 13:238-252) involves suspending phospholipids in an organic solvent which is then evaporated to dryness leaving a phospholipid film on the reaction vessel. Next, an appropriate amount of aqueous phase is added, the mixture is allowed to "swell," and the resulting liposomes which consist of multilamellar vesicles (MLVs) are dispersed by mechanical means. This technique provides the basis for the development of the small sonicated unilamellar vesicles described by Papahadjopoulos et al. (*Biochim. Biophys, Acta.*, 1968, 135:624-638), and large unilamellar vesicles.

Unilamellar vesicles may be produced using an extrusion apparatus by a method described in Cullis et al., PCT Application No. WO 87/00238, published Jan. 16, 1986, entitled "Extrusion Technique for Producing Unilamellar Vesicles" incorporated herein by reference. Vesicles made by this technique, called LUVETS, are extruded under pressure through a membrane filter. LUVETs, being usually of about 500 nm diameter or less, and frequently about 100 nm, are preferred liposomes of the instant invention. LUVETs will be understood to be included in the term "unilamellar vesicle".

Another class of liposomes are those characterized as having substantially equal lamellar solute distribution. This class of liposomes is denominated as stable plurilamellar vesicles (SPLV) as defined in U.S. Pat. No. 4,522,803 to Lenk, et al., monophasic vesicles as described in U.S. Pat. No. 4,558,579 to Fountain, et al. and frozen and thawed multilamellar vesicles (FATMLV) wherein the vesicles are exposed to at least one freeze and thaw cycle; this procedure is described in Bally et al., PCT Publication No. 87/00043, Jan. 15, 1987, entitled "Multilamellar Liposomes Having Improved Trapping Efficiencies". The teachings of these references as to preparation and use of liposomes are incorporated herein by reference.

The liposomes of this invention may be prepared in any form (e.g., SPLVs, LUVETS, MLVs, or FATMLVs noted above) so long as the diameter is about 500 nm or less and preferably about 100 nm. Liposomes with a diameter of about 500 nm or less will be termed "small liposomes". Diameter in describing a population of liposomes will be understood to reflect a range of diameters. The presence of larger liposomes intermixed with the small liposomes of this invention does not act to negate the efficacy of the small liposomes.

A variety of sterols and their water soluble derivatives have been used to form liposomes; see specifically Janoff et al., PCT Publication No. WO 85/04578, published Oct. 24, 1985, entitled "Steroidal Liposomes," Mayhew et al., PCT Publication No. WO 85/00968, published Mar. 14, 1985, described a method for reducing the toxicity of drugs by encapsulating them in liposomes comprising alpha-tocopherol and certain derivatives thereof. Also, a variety of tocopherols and their water soluble derivatives have been used to form liposomes, see Janoff et al., PCT Publication No. WO 87/02219, published Apr. 23, 1987, entitled "Alpha Tocopherol-Based Vesicles."

In the present invention, the term lipid as used herein shall mean any suitable material resulting in a bilayer such that a hydrophobic portion of the lipid material orients toward the interior of the bilayer while a hydrophilic portion orients toward the aqueous phase. Lipids further include highly hydrophobic compounds such as triglycerides, sterols such as cholesterol which can be incorporated into the bilayer. Examples of lipids are the phospholipids such as phosphatidylcholine (PC), phosphatidylethanolamine (PE), phosphatidylserine (PS), phosphatidylglycerol (PG), phosphatidic acid (PA), phosphatidylinositol (PI), sphingomyelin (SPM), and the like, alone or in combination. The phospholipids can be synthetic or derived from natural sources such as egg or soy. Useful synthetic phospholipids include dymyristoylphosphatidylcholine (DMPC) and dimyristoylphosphatidylglycerol (DMPG). Liposomes can also contain other steroid components such as polyethylene glycol derivatives of cholesterol (PEG-cholesterols), coprostanol, cholestanol, or cholestane, and combinations of PC and cholesterol. They may also contain organic acid derivatives of sterols such as cholesterol hemisuccinate (CHS), and the like. Organic acid derivatives of tocopherols may also be used as liposome-forming ingredients, such as alpha-tocopherol hemisuccinate (THS). Both CHS- and THS-containing liposomes and their tris salt forms may generally be prepared by any method known in the art for preparing liposomes containing these sterols. In particular, see the procedures of Janoff, et al., PCT Publication No. WO 85/04578, published Oct. 24, 1985, entitled "Steroidal Liposomes," and Janoff, et al., PCT Publication No. WO 87/02219, published Apr. 23, 1987, entitled "Alpha-Tocopherol Based Vesicles," filed Sept. 24, 1986, respectively. The liposomes may also contain glycolipids.

The LUVET technique begins with the preparation of liposomes by any technique such as SPLV, MLV, or FATMLV. The conventional liposomes so produced are then extruded, preferably through a filter or frit. Exemplary of such filters is the polycarbonate filter, and exemplary of such frit is the stainless steel frit. Extruder pore size, and hence LUVET size of about 500 nanometer (nm) or below was useful with below about 100 nm preferred. Extrusion was conveniently accomplished at high pressures, such as about 1000 psi.

In particular embodiments of the present invention, phosphatidylcholine such as egg or soy phosphatidylcholine may be used.

Antibody response is measured in terms of a titer of antibody (i.e., IgG or IgM). This is conveniently measured in a mouse model described below. However, the method of measuring antibody activity is not a critical element of this invention. Many methods of measuring antibody activity are known to those skilled in the art, such as radial immuno-difussion, immuno-adherence, radio-immuno assay, and compliment fixation are also useful.

It will be understood that an immunogenic amount of GM2 is that amount which will stimulate B-cells of an animal to produce immunoglobulins against GM2. This amount will vary with the potency of adjuvant, with the mode of administration and with the type and condition of animal but is easily determined by any of the well known tests for immunoglobulins with an increase in immunoglobulin representing immunogenic response.

The GM2 is present in an amount of at least about 3 ug/mg liposome lipid, and preferably at least about 10 ug and more preferably at least about 30 ug.

A pharmaceutical dosage form for humans will generally include about 50 ug GM2 to about 500 ug GM2, with 100 to 300 ug preferred. Pharmaceutical dosage form comprises the adjuvant in a pharmaceutically acceptable carrier such as physiological saline or other physiological solution. Water, or other noniso-osmotic solutions may be used if care is taken to avoid destruction of the small liposomes by osmotic pressure.

The mode of administration of the pharmaceutical dosage form may determine the sites and cells in the organism to which the compound will be delivered. Liposomes can be administered alone but will generally be administered in admixture with a pharmaceutical carrier selected with regard to the intended route of administration and standard pharmaceutical practice as noted above. While the preparations may be injected parenterally, for example, intra-arterially or intravenously, the subcutaneous rout of administration is preferred. The preparations may also be administered via oral, or intramuscular routes. For parenteral administration, they can be used, for example, in the form of a sterile aqueous solution which may contain other solutes, for example, enough salts or glucose to make the solution isotonic. Other uses, depending upon the particular properties of the preparation, may be envisioned by those skilled in the art.

In an embodiment for human use administration is subcutaneous, in about 2 to 5 doses about 2 weeks apart, and about 1 additional dose about 4 weeks thereafter. In the preferred embodiment 3 subcutaneous doses, 1 every 2 weeks and 1 additional dose 1 month thereafter is preferred. Dosage volume of about 0.1 cc is convenient but this is not critical. In subjects particularly sensitive to Lipid A toxicity (e.g., rabbits) care must be taken to use Lipid A of reduced toxicity or smaller doses of Lipid A.

"Incubation associated" refers to the spatial relationship of a substance such as GM2 or Lipid A to liposome arising from the addition and incubation of substance and liposomes. The particular spatial relationship arises from the propensity of the ganglioside or Lipid A to partition into the lipid bilayer of a preformed small liposome. This incubation associated orientation is an orientation that potentiates the immune response. This incubation association results in a distinct immunogenicity that does not arise to the same degree with encapsulation of material by a small liposome. Encapsulation will be understood to refer to incorporation of lipophilic, amphipathic, or hydrophylic compounds within the liposome at its formation.

Incubation association is accomplished by adding the component to be associated (conveniently in solution) to formed liposomes. The liposomes and component are then mixed, optionally with brief sonication (about 30 sec.), and permitted to stand for an interval. During this interval of from a few minutes to several hours, the component to be incubation associated will partition into the lipid bilayer. In the preferred embodiment the mixture is permitted to stand for about ½ to 1 hour for partitioning of the added components, but this interval is not critical.

The process is generally not pressure sensitive, and atmospheric pressure is convenient. Depending on the stability of the liposomes and the added components any temperature may be used which will not be destructive, conveniently about 15° to 25° C. In one embodiment, the composition is then dried, by any convenient method such as rotoevaporation. With labile products this may be done at reduced temperature. The dry material is then reconstituted to a convenient concentration with an aqueous solution prior to use. In the preferred embodiment reconstitution is accomplished with phosphate buffered saline. Tests of the supernatant of reconstituted material in a test model indicated that the GM2 was not free in solution.

Small liposome-Lipid A-GM2 combinations of a size range of about 500 nm or less produce more immunogenic response than the larger liposomes, with those of about 100 nm being preferred.

Referring to TABLE 1 the properties of the instant composition will be easily understood. Vaccine Groups #1, 2, and 3 employ egg phosphatidylcholine small liposomes (unilamellar vesicles) of about 100 nm and 5 ug of incubation associated MP Lipid A/mg liposome lipid and with 30, 10, and 3.3 ug of incubation associated GM2/mg liposome lipid, respectively. Each group consisted of 5 mice of about 40 to 60 gms injected with the composition subcutaneously in 0.1 cc of pharmaceutically acceptable carrier, here phosphate buffered saline. Furthermore each mouse received 50 ug of GM2 of the form designated. For groups #1, 2, and 3 all mice responded with at least a titer increase of 1/20. Group #1, however, displayed the most marked increase in titer of 1/320 in 4 out of five animals.

Group #4 reports the results of an egg phosphatidylcholine (EPC) unilamellar vesicle with 5 ug MP Lipid A/mg liposome lipid encapsulated (not incubation associated) within the lipid, and 50 ug encapsulated GM2/mg liposome lipid. Four animals showed minimal response, but the response was substantially below that of incubation associated small liposomes.

Group #5 reports EPC unilamellar vesicle further containing 1 mg phosphatidic acid/9 mg egg phosphatidylcholine, imparting a charge to the liposome, 5 ug of MP Lipid A, and 50 ug of GM2/mg lipid, both the Lipid A and GM2 being encapsulated and not incubation associated. The increase in antibody titer in the 4 animals responding is significant but less pronounced than the increase from small liposomes with incubation associated Lipid A and GM2 of Groups #1-3.

Other liposomal formulations, of nonsmall nonincubation associated immuno-potentiator gave significantly less pronounced and less consistent test responses.

Groups #6, 7, and 8 report GM2 alone, GM2 adsorbed to Salmonella, and GM2 in complete Freunds adjuvant, respectively, all absent Lipid A. Immunogenic response was seen to be inconsistent and minimal.

ANALYTICAL PROCEDURE

IgM Titer Determination

IgM determination was performed on female BALB/c-C57BL/6 $F_1$ (B6) mice, 2 to 5 mo. of age (The Jackson Laboratory, Bar Harbor, Me.).

In each test of a vaccine, five mice were immunized with a given vaccine. Mice were selected randomly from the same shipment. Vaccines were administered subcutaneously in a total vol of 0.1 ml per mouse. Two vaccinations containing 50 ug of GM2 were given at 1 mo. intervals. Mice were bled from the retro-orbital sinus at 2 wk intervals after vaccination, and serum samples for serological testing (approximately 0.1 ml) were stored at −20° C.

These samples were then tested by either the Enzyme Linked Immunosorbent Assay (ELISA) or Immune Adherence Assay. In the ELISA Assay, ganglioside GM2 was serially diluted twofold in microtest titration plates, starting at 5 ug/well. The plates were air-dried for 2 hours and blocked with 1% BSA for 2 hours. Dilutions of test sera were added to each well, and the plates were incubated for 1 hour at room temperature. The plates were washed and the second antibody, anti-mouse IgM (u-specific for detection of IgM antibodies), and anti-mouse ($\gamma$-specific for IgG) conjugated with alkaline phospatase (Sigma Chemical Corp., St. Louis, Mo.) was added at a dilution of 1:200. The plates were incubated for 45 minutes and washed. Diethanolamine substrate was added and the plates were incubated for 20 minutes at 37° C. The reaction was measured by absorbance at 414 nm on an ARTEC (ARTEC Labs Corp., N.Y.) reader. Absorbance readings on tested sera were corrected by subtracting the absorbance obtained for negative control sera. Dilutions of test sera re scored as positive if the corrected absorbance at 414 nm was greater than 0.19.

EXAMPLE 1

Unilamellar Vesicle with Encapsulated Lipid A and GM2

Liposomes with encapsulated GM2 and Lipid A were prepared at atmospheric pressure and ambient temperature (20°-25° C.) by pipetting 875 ul of EPC at 100 mg/ml (8.75 mg) into a 100 ml round bottom flask, to which was added 175 ul of Lipid A at 2 mg/ml (350 ug), and 700 ug of brain ganglioside. This mixture was evaporated to dryness with a rotoevaperator. To the residue was added 1.4 ml of phosphate buffered saline and the mixture vortexed until all lipid was removed from the walls of the flask and liposomes formed, about 3 min. The mixture, with encapsulated GM2 and Lipid A was permitted to stand for 2 hours at ambient temperature.

The mixture was then placed in 1.5 ml cryotubes, filling each tube about ½ full. These tubes ware frozen and thawed 5 times by placing alternately in liquid nitrogen and 36° C. bath, resulting in FATMLVs of Group #4 of Table 1. However ½ of this material was further processed to become the material of Group #5.

EXAMPLE 2

Small Unilamellar Vesicle with Encapsulated Lipid A and GM2

The unsized FATMLVs of Example 1 were passed through a 0.1 um stainless steel frit 10 times. The final concentration of small liposomes so produced was 50 mg/ml EPC, 250 ug/ml Lipid A, and 500 ug/ml brain ganglioside. These small liposomes were used in Group #5 of Table 1.

EXAMPLE 3

Small Unilamellar Vesicle with Incubation Associated Lipid A and GM2

The incubation associated liposomes of Groups #1, 2, and 3 were prepared with 300 mg (3.0 ml) of egg phosphatidylcholine added to a round bottomed flask and dried by rotoevaporation. 6 ml of phosphate buffered saline was added to the dried lipid and vortexed until all lipid was removed from the walls of the flask and liposomes formed, about 3 min. The resulting liposomes were passed 1 time through 2 filters (Nucleopore, Pleasenton, Calif.) each of 0.4 um and 1 time through 2 filters of 0.2 um and 10 times through 2 filters of 0.1 um using a 10 ml LUVET apparatus (Lipex Biomembrane, Vancouver, B.C.). The resulting small liposomes were stored under nitrogen gas prior to incubation association.

The 500 ug GM2 and 250 ug Lipid A (in organic solvent) to be incubation associated were added to a round bottomed flask and dried. Incubation association was accomplished by combining resuspending the Lipid A and GM2 in 1 ml of phosphate buffered saline and vortexing for 30 sec. To this was added varying amounts of the small liposomes, and the mixture then being permitted to stand at 25° C. for ½ to 1 hour. For Group #1 1 mg of small liposome lipid was added/50 ug GM2, for Group #2 1 mg small liposome lipid/10 ug GM2, and for Group #3 1 mg liposome lipid/3.3 ug GM2. The resulting material was small liposomes with incubation associated Lipid A and GM2.

Augmenting the Immunogenicity of GM2

TABLE 1

| IgM ANTI-GM2 ELISA IN MICE FOUR (4) WEEKS AFTER A SECOND VACCINATION | | | | |
|---|---|---|---|---|
| Anti-GM2 Vaccine Groups | GM2 (ug) Lipid (mg) | No. Mice Vaccinated | No. Mice Responding (titer >1/20) | IgM Titer |
| EPC:Uni #1 INCUBATION ASSOCIATED | 30 | 5 | 5 | 320[1] 320 80 320 320 |
| EPC:Uni #2 INCUBATION ASSOCIATED | 10 | 5 | 5 | 80[1] 320 320 80 320 |
| EPC:Uni #3 INCUBATION ASSOCIATED | 3.3 | 5 | 5 | 320[1] 80 80 80 320 |
| EPC:Uni #4 | 50 | 5 | 4 | 40[2] 80 80 80 |
| EPC/PA:Uni #5 | 50 | 5 | 4 | 40[2] |

TABLE 1-continued

IgM ANTI-GM2 ELISA IN MICE FOUR (4) WEEKS AFTER A SECOND VACCINATION

| Anti-GM2 Vaccine Groups | GM2 (ug) Lipid (mg) | No. Mice Vaccinated | No. Mice Responding (titer >1/20) | IgM Titer |
|---|---|---|---|---|
| | | | | 40 |
| | | | | 160 |
| | | | | 160 |
| GM2 ALONE #6 | — | 5 | 1 | 40[2] |
| GM2 ADSORBED TO SALMONELLA #7 | — | 5 | 2 | 40[2] 80 |
| GM2 in COMPLETE FREUNDS ADJUVANT #8 | — | 5 | 1 | 80[2] |

1. IgM anti-GM2 titer determined by ELISA.
2. IgM anti-GM2 titer determined by Immune Adherence Assay.

We claim:

1. A composition comprising liposomes of diameter less than about 500 nm, an incubation associated immuno-potentiator and an incubation associated ganglioside antigen, both associated with said liposomes.

2. The composition of claim 1 wherein said liposomes are about 100 nm in diameter.

3. The composition of claim 1 wherein the liposomes are unilamellar vesicles.

4. The composition of claim 1 wherein said liposomes comprise phosphatidylcholine.

5. The composition of claim 1 wherein the ganglioside antigen is GM2, GD2, or GD3.

6. The composition of claim 5 wherein the ganglioside antigen is GM2.

7. The composition of claim 6 wherein the GM2 is present in an amount of at least about 3 ug/mg liposome lipid.

8. The composition of claim 7 wherein the GM2 is present in an amount of at least about 10 ug/mg liposome lipid.

9. The composition of claim 8 wherein the GM2 is present in an amount of at least about 30 ug/mg liposome lipid.

10. The composition of claim 6 in a pharmaceutical dosage form comprising about 50 to about 500 ug GM2.

11. The composition of claim 10 in a pharmaceutical dosage form comprising about 100 to about 300 ug GM2.

12. The composition of claim 1 wherein the immuno-potentiator is Lipid A.

13. The composition of claim 12 wherein the Lipid A is present in at least about 5 ug/mg liposome lipid.

14. The composition of claim 13 wherein the Lipid A is present in at least about 25 ug/mg liposome lipid.

15. The composition of claim 12 wherein said liposomes comprise phosphatidylcholine.

16. A composition prepared by the process of combining by incubation association liposomes of diameter less than about 500 nm, an immuno-potentiator and a ganglioside antigen.

17. The composition of claim 16 wherein the ganglioside antigen is GM2, GD2, or GD3.

18. The composition of claim 17 wherein the ganglioside antigen is GM2.

19. The composition of claim 16 wherein the immuno-potentiator is Lipid A.

20. A method of preparing an adjuvant composition comprising combining by incubation association liposomes of diameter less than about 500 nm, an immuno-potentiator and a ganglioside antigen.

21. The method of claim 20 wherein the ganglioside antigen is GM2, GD2, or GD3.

22. The method of claim 20 wherein the liposomes are unilamellar vesicles.

23. The method of claim 20 wherein the immuno-potentiator is Lipid A.

24. A method of augmenting an immune response in an animal comprising administering to said animal an adjuvant composition comprising liposomes of diameter less than about 500 nm, an incubation associated immuno-potentiator and an incubation associated ganglioside antigen, both associated with said liposome.

25. The method of claim 24 wherein the ganglioside antigen is GM2, GD2, or GD3.

26. The method of claim 24 wherein the immuno-potentiator is Lipid A.

27. The method of claim 26 wherein the Lipid A is present in at least about 5 ug/mg liposome lipid.

28. The method of claim 27 wherein the Lipid A is present in at least about 25 ug/mg liposome lipid.

29. A composition comprising liposomes of about 100 nm in diameter, incubation associated monophosphoryl Lipid A present in at least about 5 ug/mg liposome lipid and incubation associated GM2 present in at least about 3 ug/mg liposome lipid, both associated with said liposomes.

* * * * *